US00RE41209E

(19) United States
(12) Reissued Patent
Murrer

(10) Patent Number: US RE41,209 E
(45) Date of Reissued Patent: Apr. 6, 2010

(54) PLATINUM COMPLEXES

(75) Inventor: Barry Murrer, Reading (GB)

(73) Assignees: Genzyme Corporation, Cambridge, MA (US); The Institute of Cancer Research, London (GB)

(21) Appl. No.: 12/437,889

(22) Filed: May 8, 2009

Related U.S. Patent Documents

Reissue of:
(64) Patent No.: 5,665,771
Issued: Sep. 9, 1997
Appl. No.: 08/597,953
Filed: Feb. 7, 1996

(51) Int. Cl.
*A61K 31/28* (2006.01)
*C07F 15/00* (2006.01)

(52) U.S. Cl. ..... 546/2; 556/137; 546/10; 514/492

(58) Field of Classification Search ..... 556/137; 541/6, 492; 546/2, 10
See application file for complete search history.

(56) References Cited

U.S. PATENT DOCUMENTS

| | | | | | |
|---|---|---|---|---|---|
| 3,892,790 | A | | 7/1975 | Tobe et al. | |
| 4,533,502 | A | | 8/1985 | Rochon et al. | |
| 4,760,155 | A | * | 7/1988 | Heffernan et al. | 556/136 |
| 5,519,155 | A | * | 5/1996 | Barnard et al. | 556/137 |
| 6,518,428 | B1 | * | 2/2003 | Wong et al. | 546/2 |
| 7,122,668 | B2 | * | 10/2006 | Barenholz et al. | 544/137 |
| 7,589,225 | B2 | * | 9/2009 | Du Preez | 556/137 |
| 2007/0082882 | A1 | * | 4/2007 | Farrell | 514/184 |

FOREIGN PATENT DOCUMENTS

| | | | | |
|---|---|---|---|---|
| EP | 0 115 929 | A1 | * | 8/1984 |
| EP | 0 199 524 | A2 | * | 10/1986 |
| EP | 0 199 524 | A3 | * | 10/1986 |
| EP | 0 199 524 | | * | 10/1986 |
| EP | 0 273 515 | A1 | * | 7/1988 |
| EP | 0 328 274 | A1 | * | 8/1989 |
| EP | 0 503 830 | A1 | * | 9/1992 |
| EP | 0 333 351 | A3 | * | 9/1999 |
| WO | WO 95/07698 | | * | 3/1995 |

OTHER PUBLICATIONS

Hollis et al., J. Med. Chem., 32:128–136 (1989).*
Chemical Abstracts, 109:242998 (1988); 105:219014 (1986); 103:226258 (1985).*
L. Steven Hollis et al., "Chemical and Biological Properties of a New Series of Cis–Diammineplatinum (ll) Antitumor Agents containing Three Nitrogen Donors: cis–[Pt(NH3)2(N–donor)Cl]+", Journal of medicinal Chemistry, vol. 32, No. 1, 1986, pp. 128–136.*
Chemical Abstracts, 78–Inorganic Chemistry, vol. 121:314429, 1994, p. 1055.*
Chemical Abstracts, 78–Inorganic Chemistry, vol. 103:226260, 1995, p. 725.*
Rochon et al, Inorganic Chemistry, vol. 30, No. 24, pp. 4531–4535 (1991).*
Abrams et al., Inorganica Chimica Acta (1987) 131:3–4.
Braddock et al., Chem.–Biol. Interactions (1975) 11:145–164.
Dhara, Indian J. Chem. (1970) 8:193–194.
Dupont et al., Polyhedron (1994) 13(17):2583–2587.
Giandomenico et al., Inorg. Chem. (1995) 34:1015–1021.
Ivanova, J. Inorg. Chem. (1957) ll(6):1317–1323.
Kong and Rochon, Can. J. Chem. (1978) 56:441–445.
Pfeffer et al., Spectrochimica Acta (1974) 30A:331–340.
Pfeffer et al., Spectrochimica Acta (1974) 30A:341–355.
Rochon and Fleurent, Inorganica Chimica Acta (1988) 143:81–87.
Rochon and Kong, Can. J. Chem. (1986) 64:1894–1896.
Tobe and Khokhar, Wadley Medical Bulletin (1977) 7(1):114–137.

* cited by examiner

*Primary Examiner*—Porfirio Nazario Gonzalez
(74) *Attorney, Agent, or Firm*—Morrison & Foerster LLP

(57) ABSTRACT

Platinum complexes of formula Ia or Ib

Ia

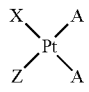

Ib

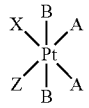

where each A, is a leaving group and may be the same or different, which is suitably halo, especially chloro, hydroxy, carboxylate or together form a bi-dentate carboxylate or sulphate, each B, which may be the same or different, is halo, hydroxy, carboxylate, carbamate or carbonate ester, Z is a substituted amine wherein the substituent sterically hinders access of the Pt atom to a DNA strand of a tumour cell, and X is $NH_3$ or mono- or di-alkyl substituted $NH_3$, are active against cancer cells, and appear to show a unique form of chemical and biological action.

15 Claims, No Drawings

PLATINUM COMPLEXES

Matter enclosed in heavy brackets [ ] appears in the original patent but forms no part of this reissue specification; matter printed in italics indicates the additions made by reissue.

The present invention concerns improvements in platinum complexes, and particularly concerns novel platinum complexes having activity against cancer cells.

The activity of a Pt(II) complex, cisplatin, $[PtCl_2(NH_3)_2]$, against cancer cells was discovered some twenty years ago, and this complex has become a major pharmaceutical. However, cisplatin has long been known to suffer from two major drawbacks; namely, its severe toxicities (especially nephrotoxicity, nausea and vomiting and neurotoxicity) and the propensity of many tumours to exhibit resistance (either intrinsically or acquired after an initial promising response). Many platinum complexes have been studied in an attempt to overcome the limitations of cisplatin.

The present invention provides a cis-platinum complex of general formula Ia or Ib Ia

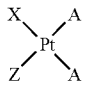

Ib

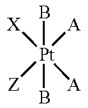

where each A, is a leaving group and may be the same or different, which is suitably halo, especially chloro, hydroxy, carboxylate or together form a bi-dentate carboxylate or sulphate, each B, which may be the same or different, is halo, hydroxy, carboxylate, carbamate or carbonate ester, Z is a substituted amine wherein the substituent sterically hinders access of the Pt atom to a DNA strand of a tumour cell, and X is $NH_3$ or mono- or di-alkyl substituted $NH_3$.

Preferably the complex is of formula Ia.

Particularly, we have found that where Z is an unsaturated cyclic amine, where the ring may contain one or more other hetero-atoms, and most especially where Z is pyridine, and where Z has a substituent on the atom adjacent to the amine nitrogen atom, the complex appears to be sterically hindered.

The cyclic amine may be a 5- or 6-membered monocyclic or 8 to 10-membered polycyclic amine, especially bicyclic, for example fused ring systems where the amine is co-ordinated through the nitrogen atom of a pyridine ring. In the case of such bicyclic fused ring systems, the other ring may be phenylene or may contain one or more heteroatoms, especially nitrogen or oxygen.

In the case of substituted cyclic amines, the substituent may be lower alkyl or alkoxy of 1 to 4 carbon atoms, (especially methyl or methoxy), halo, (especially chloro or bromo), or aryl, (especially benzyl). The substituent may itself be substituted by lower alkyl or halo. By the term "lower alkyl" is meant an alkyl group with from 1 to 6 carbon atoms. The cyclic amine may carry other substituents either adjacent to the coordinating nitrogen atom or elsewhere on the ring. Other substituents include electron-withdrawing or electron-donating substituents such as nitro and alkoxy eg methoxy. If the cyclic amine is a fused ring system where the fused ring is an aromatic ring in positions 2 and 3 of the cyclic amine, no other substituent is necessary, although a substituent may be present.

The leaving groups A may be selected from those well known to those skilled in the art.

Preferably, each A is the same, and is chloro, or together form cyclobutane-1,1-dicarboxylate or sulphate. In the case of Pt(IV) complexes of formula Ib, preferably each B is the same, and preferably is hydroxy.

We have demonstrated that members of this novel class of sterically hindered complexes exhibit different chemical characteristics from analogues which are not hindered, and they exhibit a different biological profile. Tests relating to these characteristics are described below.

The complexes of formula Ia and Ib are novel and may be prepared by methods analogous to those described in the art. For example, general preparations of platinum complexes with mixed ammine/alkylamine ligands are given by P D Braddock et al Chem. Biol. Interactions 1975, II, 145. We refer also to EP 328274 (Johnson Matthey).

The requisite starting materials are themselves known.

The complexes of the invention demonstrate activity against cancer cells in vitro; some complexes have also been tested in vivo and have also demonstrated interesting activity. The complexes appear to show a different activity, particularly towards cancer cells which are resistant to treatment with cisplatin, to the existing commercial platinum anticancer complexes and therefore the complexes are indicated for use in the treatment of tumours.

According to a further aspect of the invention, there is provided a complex of formula Ia or Ib for use in medicine and in particular for use in the treatment of cancer. A still further aspect of the invention provides the use of a complex of formula Ia or Ib in the manufacture of a medicament for the treatment of cancer. Alternatively, there is provided a method of treating cancer comprising administering to a patient in need thereof a pharmaceutically effective amount of a complex of formula Ia or Ib.

The active complexes may be administered in the form of pharmaceutical compositions formulated according to well known principles. Thus, a still further aspect of the present invention provides a pharmaceutical composition comprising a compound of formula Ia or Ib in admixture with a pharmaceutically acceptable diluent or carrier and optionally one or more other therapeutic agents. Such compositions may be in the form of solutions or suspensions for injection, or to be in capsule, tablet, dragee, or other solid composition or as a solution or suspension for oral administration, or formulated into pessaries or suppositories, or sustained release form of any of the above. Suitable diluents, carriers, excipients and other components are known. It may be desirable also to formulate a composition for topical administration such as an ointment or cream, or to be administered as a transdermal patch.

The pharmaceutical compositions according to the invention may contain dosages determined in accordance with conventional pharmaceutical methods, suitably to provide active compounds in the dosage range in humans of from 0.1 to 100 mg/kg body weight per day, in a single unit dose or in a number of smaller unit doses. Preferred dosage ranges are 1 to 30 mg/kg body weight per day.

The complexes of the invention may be administered alone or in combination with another chemotherapeutic agent, such as cisplatin, either as a single treatment or course of treatment or as part of combined therapy with other pharmaceuticals to overcome or diminish side effects or to improve bio-availability, or in combination with other therapies such as radiation treatment.

Without wishing to be bound by any theory, it appears to the inventors that the complexes of the invention exhibit increased selectivity towards DNA in cancer cells compared to unhindered analogues, especially cisplatin. It has been reported by Tobe et al (Wadley Medical Bulletin 7, 1, 114–135) that steric effects of bulky substituents close to the platinum atom have a profound effect upon the rate of substitution reactions there. At that time no systematic study of the way in which variation of the substituent on the primary amine affects the rate and extend of bonding of the Pt complex to DNA had been undertaken. There is no evidence as to whether such effects could be beneficial or detrimental to the antitumour activity of platinum complexes. The present invention introduces steric hindrance as close as possible to the platinum atom by the use of substituted heterocyclic ligands, rather than amines, and we believe that the complexes of the invention show unexpected benefits. In particular, the complexes of the invention exhibit reduced resistance factors (resistance factor is the ratio of the activity of a complex against a parent line of cancer cells to the activity against a derivative of that cell line which has developed resistance to cisplatin). For example, in the CH1 xenograft (Institute of Cancer Research, Sutton, Surrey) which is derived from cell line sensitive to cisplatin, cisplatin shows significant activity at the maximum tolerated dose, however the tumour does grow back. The novel complex [$PtCl_2(NH_3)$(2-methylpyridine)] shows slightly less potency, meaning that a greater dose is required than cisplatin, but the complex exhibits a curative effect, and the tumour does not grow back.

We believe that cisplatin, and all known anti-tumour active Pt complexes, bind to DNA in cancer cells, causing cross-linking of DNA strands. Approximately 10% of the total links are interstrand cross-links. Our tests with certain of the complexes of the invention indicate that there is no detectable cross-linking between strands. This indicates a different mechanism of action.

The invention will now be described with reference to the following preparative examples.

EXAMPLE 1

(SP-4-3)-amminedichloro(2-methylpyridine) platinum(II)

KCl (2.2 g, 29.5 mmol) and K[$PtCl_3(NH_3)$] (10 g, 28 mmol) were dissolved in water (100 ml) and stirred during the addition of KI (13.90 g, 84 mmol) in water (15 ml). 2-methylpyridine (2.8 g, 30 mmol) was then added. After 3 hours stirring, the yellow precipitate of (SP-4-3)-amminediiodo(2-methylpyridine)platinum(II) was collected by filtration, washed with water and then methanol and dried in vacuo, yield 8.06 g. The solid was added to a stirred solution of $AgNO_3$ (4.78 g, 28.1 mmol) in water (50 ml) and stirring continued for 6 hours in the dark. After filtration to remove silver halides, the filtrate was treated with concentrated HCl (4.5 ml, ca. 49.5 mmol) and stirred for 3 days. The resulting pale yellow solid was collected by filtration, washed with water than acetone, and dried in vacuo to give (SP-4-3)-amminedichloro(2-methylpyridine)platinum(II) (5.78 g, 52%), Found: C 19.4, H 2.7, N 7.3, Cl 18.9%; $C_6H_{10}N_2Cl_2Pt$ requires C 19.5, H 2.7, N 7.4, Cl 18.9%.

Using analogous procedures, the following compounds were prepared:

| | Ligand Z | % yield | Microanalysis % found (expected) C | H | N | Cl |
|---|---|---|---|---|---|---|
| Example 2 | 2-ethylpyridine | 41 | 21.5 (21.5) | 3.2 (3.1) | 7.3 (7.2) | 18.0 (18.2) |
| Example 3 | 2-methylquinoline | 17 | 28.4 (28.0) | 3.0 (2.8) | 6.5 (6.5) | 16.6 (16.6) |
| Example 4 | 2,4-dimethyl-pyridine | 37 | 21.4 (21.5) | 3.2 (3.1) | 7.1 (7.2) | 18.1 (18.2) |
| Example 5 | 2-isopropylpyridine | 48 | 23.9 (23.8) | 3.6 (3.5) | 6.8 (6.9) | 17.3 (17.6) |
| Example 6 | 2,6-dimethyl-pyridine | 14 | 21.5 (21.5) | 2.85 (3.1) | 7.3 (7.2) | 18.4 (18.2) |

EXAMPLE 7

(OC-6-43)-amminedichlorodihydroxo(2.4-dimethylp.vridine)platinum(IV)

The product of Example 4, [(SP-4-3)-amminedichloro(2,4-dimethylpyridine)platinum(II)], (2.0 g), heptane (5 ml), water (2.9 ml) and $H_2O_2$ (30% w/v 2.9 ml) were stirred vigorously and refluxed for 2 hours. On cooling, the yellow solid was collected by filtration, washed with $H_2O$ and dried to give (OC-6-43)-amminedichlorodihydroxo(2,4-dimethylpyridine)platinum(IV) (1.74 g, 77%). Found C 19.77, H 3.03, N 6.52, Cl 16.57%, $C_7H_{14}N_2Cl_2O_2Pt$ requires C 19.81, H 3.30, N 6.60, Cl 16.75%.

EXAMPLE 8

(OC-6-43)-amminebisbutyratodichloro(2.4-dimethylpyridine)platinum(IV)

The product of Example 7 (OC-6-43)-amminedichlorodihydroxo(2,4-dimethylpyridine)platinum (IV) (1.5 g) was suspended in butyric anhydride (5.6 g) and stirred at room temperature for 3 days. The pale yellow solid was collected by filtration, washed thoroughly with MeOH and dried in vacuo to give (OC-6-43)-amminebisbutyratodichloro(2,4-dimethylpyridine)platinum (IV) (1.17 g). Found C 31.4, H 4.5, N 4.9, Cl 12.5; $C_{15}H_{26}N_2O_4Cl_2Pt$ requires C 31.9, H 4.6, N 5.0, Cl 12.6%.

EXAMPLE 9 ammine(cyclobutane-1.1-dicarboxylato)(2.4-dimethylpyridine)platinum(II)

2,4-dimethylpyridine (1.65 g) was added to a solution of K[$PtCl_3(NH_3)$] (5.0 g), KCl (1.1 g) and KI (6.95 g) in water (60 ml). After 3 hours stirring at room temperature the yellow precipitate was collected by filtration, washed with water and then methanol and dried in vacuo. This compound was added to a solution of $AgNO_3$ (2.94 g, 1.95 mmol) in water (30 ml) and acetone (5 ml) and stirred in the dark for 5 hours. The mixture was filtered to remove silver halides and the flitrate was added dropwise to a warm (60° C.) solution of dipotassium cyclobutane-1,1-dicarboxylate (13.2 mmol). The solution was kept at 60° C. for 2 hours, then left at room temperature overnight. The solvent was removed in vacuo and the white solid dissolved in the minimum amount of warm EtOH, filtered and stored at −20° C. After 4 hours a white crystalline material was filtered off, washed with cold ethanol and dried (yield 0.81 g). NMR indicated the desired compound, together with ca 0.9 mol EtOH/Pt. (NMR, $CD_3OD$ δ 8.7 d (1H), 7.3 s (1H), 7.1 d (1H), 3.6 q ($CH_3CH_2OH$), 3.1 S (3H), 2.9 m (4H), 2.4 s (3H), 1.9 m (2H), 1.2 t ($CH_3CH_2OH$). Microanalysis found C 34.8, H 5.1, N 5.3, $C_{13}H_{18}N_2O_4Pt$. 0.9 EtOH requires C 35.3, H 4.7, N 5.6%. IR 1629 $cm^{-1}$ (bound carboxylate).

The complexes of the invention were tested against human cancer cell lines grown in cell culture according to established testing procedures (described by Kelland et al, Cancer Research 53, 2581–2586, June 1993). The results are shown below in Table 1, in comparison with the commercial complexes cisplatin and carboplatin. The results are given in concentrations (μM) necessary to achieve a 50% decrease in cell proliferation, with resistance factors in brackets for the cisplatin-resistant cell lines. HX62 and SKOV3 are inherently resistant to cisplatin, and the cell lines bred to be resistant to cisplatin have the designation R, as in 41MR. Resistance factors for HX62 and SKOV3, for which there is no sensitive counterpart, have been derived by dividing by the $IC_{50}$ for the 41M line, an inherently cisplatin sensitive line.

It is not, of course, surprising that the resistance factors for cisplatin itself are fairly high, but it can be seen that the other commercial complex, carboplatin, is also less effective with cisplatin-resistant cell lines. The complexes of the invention appear to show reduced resistance factors compared to the commercial substances, and this is assessed as being advantageous.

TABLE 1

| Compound | HX62 | SKOV3 | 41M | 41MR | CH1 | CH1R | A2780 | A2780R |
|---|---|---|---|---|---|---|---|---|
| Cisplatin | 15.5 (37.8) | 4.3 (10.5) | 0.41 | 1.9 (4.6) | 0.12 | 0.44 (3.7) | 0.35 | 7.8 (22) |
| Carboplatin | 85 (26) | 37.7 (11) | 3.3 | 8.8 (2.7) | 1.3 | 6 (4.6) | 2.6 | 37.4 (14) |
| Example 1 | 40 (9.8) | 17.5 (4.3) | 4.1 | 5 (1.2) | 1.9 | 3.7 (1.9) | 1.28 | 4.4 (3.4) |
| Example 2 | 36 (10) | 20 (2.9) | 3.4 | 5.7 (1.7) | 1.4 | 3.6 (2.6) | 4.4 | 11.0 (2.5) |
| Example 4 | 4.9 (1) | 14.0 (3) | 4.25 | 1.9 (0.4) | 2.3 | 5.3 (2.3) | 6.6 | 18.0 |
| Example 5 | 49 (8) | 20 (3.3) | 6.1 | 5.6 (0.9) | 2.4 | 4.2 (1.7) | 3.9 | 14 (3.6) |
| Example 6 | 62 (2) | 46 (1.4) | 33 | 28 (0.84) | 20 | 35 (1.74) | 35 | 77 (2.2) |
| Example 7 | 72 (9) | 47 (5.9) | 8 | 17.5 (2.2) | 3.1 | 8.9 (2.5) | 14 | 30 (2.1) |

The compound of Example 1 was used for toxicological studies and pharmacological studies in Balb C mice.

The results are given in Table 2.

TABLE 2

| | EXAMPLE 1 | | | CISPLATIN | | |
|---|---|---|---|---|---|---|
| TUMOUR | $LD_{50}$ | $ED_{90}$ | TI | $LD_{50}$ | $ED_{90}$ | TI |
| ADJ/PC6 | | | | | | |
| Single dose (i.p.) | 43 | 3 | 14.3 | 11.3 | 1.6 | 7.1 |
| Single dose (p.o.) | 560 | 6.2 | 90.3 | 140 | 24 | 5.8 |
| Daily × 5 (i.p.) | 21 | 0.8 | 26.3 | 2.4 | 0.2 | 11.7 |

$LD_{50}$ (mg/kg); dose causing 50% lethality
$ED_{90}$ (mg/kg); dose required to reduce tumour mass by 90%
TI, therapeutic index; $LD_{50}/ED_{90}$.

No significant histological evidence of liver, kidney, spleen, gastrointestinal tract, brain or skin toxicity was observed in mice receiving a $LD_{10}$ dose of the compound of Example 1. There were no significant differences in levels of alkaline phosphatase (ALP), alaninc aminotransferase (ALT), the gut disaccharides, maltose, sucrose and trehalose, and urea and creatinine in treated mice ($LD_{50}$ dose) compared to control mice.

We claim:

1. A cis-platinum complex of general formula Ia or Ib

Ia

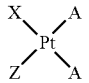

Ib

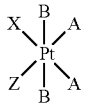

where each A, is a leaving group and may be the same or different, or together form a bi-dentate carboxylate or sulphate, each B, which may be the same or different, is halo, hydroxy, carboxylate, carbamate or carbonate ester, Z is a substituted *unsaturated cyclic* amine *coordinated to Pt through the amine nitrogen atom which amine may contain one or more other heteroatoms, wherein the amine is substituted by lower $C_1$–$C_4$ alkyl or alkoxy adjacent to the amine nitrogen atom,* wherein the substituent sterically hinders access of the Pt atom to a DNA strand of a tumour [ceil] *cell*, and X is $NH_3$ [or mono- or di-alkyl substituted $NH_3$].

2. A complex according to claim 1, wherein Z is a 5- or 6-membered monocyclic or a 8 to 10-membered polycyclic tertiary amine.

3. A complex according to claim 1, wherein Z is a substituted pyridine or a bicyclic amine where the amine is coordinated through the nitrogen atom of a pyridine ring.

4. A complex according to claim 1, wherein Z is a pyridine substituted by [lower alkyl or alkoxy] *methyl* in the 2 position.

5. A complex according to claim 4, wherein each A is [halo, hydroxy, carboxylate or together form bi-dentate carboxylate or sulphate] *chloro*.

6. A cis-platinum complex selected from the group consisting of (SP-4-3)-amminedichloro(2-methylpyridine) platinum (II); (SP-4-3)-amminedichloro(2-ethylpyridine) platinum(II); (SP-4-3)-amminedichloro(2 -methylquinoline) platinum(II); (SP-4-3)-amminedichloro(2,4-dimethylpyridine) platinum(II); (SP -4-3)-amminedichloro(2-isopropylpyridine) platinum(II); (SP-4-3)-ammine-dichloro(2,6-dimethylpyridine) platinum(II); (OC-6-43)-amminedichlorodihydroxo-(2,4-dimethylpyridine) platinum(IV); (OC-6-43)-aminebisbutyratodichloro(2,4-dimethylpyridine) platinum(IV); and ammine(cyclobutane-1,1-dicarboxylato) (2,4-dimethylpyridine) platinum (II).

7. A pharmaceutical composition comprising as active ingredient a complex according to claim [1] *5*, in admixture with a pharmaceutically acceptable diluent or carrier and optionally one or more other therapeutic agents.

8. A composition according to claim 7, in unit dosage form.

9. A composition according to claim 7 or 8 for oral administration.

10. A method of treating cancer [compsiring] *comprising* administering to a patient in need thereof a pharmaceutically effective amount of a complex according to claim [1] *5*.

*11. The cis-platinum complex of claim 6, that is (SP-4-3) amminedichloro(2-methylpyridine)platinum (II).*

*12. A pharmaceutical composition comprising the complex according to claim 11, in admixture with a pharmaceutically acceptable diluent or carrier and optionally one or more other therapeutic agents.*

*13. The composition according to claim 12, in unit dosage form.*

*14. The composition according to claim 12 or 13, adapted for oral administration.*

*15. A method of treating cancer comprising administering to a patient in need thereof a pharmaceutically effective amount of the complex of claim 11.*

* * * * *